United States Patent
Tsuji et al.

(10) Patent No.: US 6,900,364 B2
(45) Date of Patent: May 31, 2005

(54) METHOD OF RECOVERING CUMENE

(75) Inventors: Junpei Tsuji, Ichihara (JP); Masaaki Katao, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 95 days.

(21) Appl. No.: 10/471,664

(22) PCT Filed: Mar. 7, 2002

(86) PCT No.: PCT/JP02/02101

§ 371 (c)(1),
(2), (4) Date: Sep. 12, 2003

(87) PCT Pub. No.: WO02/072507

PCT Pub. Date: Sep. 19, 2002

(65) Prior Publication Data

US 2004/0087821 A1 May 6, 2004

(30) Foreign Application Priority Data

Mar. 14, 2001 (JP) .......................... 2001-71782

(51) Int. Cl.$^7$ .................................................. C07C 4/24
(52) U.S. Cl. ..................................................... 585/476
(58) Field of Search ......................................... 585/476

(56) References Cited

PUBLICATIONS

J.L. Faria et al., "Photochemistry of 2,3–dimethyl–2, 3–diphenylbutane: carbon–carbon homolysis and protonation–induced side–chain fragmentation", *J. Phys. Chem.*, vol. 96, No. 26 (1992), pp. 10869–10874.

*Primary Examiner*—Thuan D. Dang
(74) *Attorney, Agent, or Firm*—Sughrue mion, PLLC

(57) ABSTRACT

A process for recovering cumene, characterized by subjecting 2,3-dimethyl-2,3-diphenylbutane produced in a process in which cumene is used, to hydrogenolysis in the presence of a catalyst thereby to convert it into cumene, and recovering the cumene.

4 Claims, No Drawings

METHOD OF RECOVERING CUMENE

TECHNICAL FIELD

The present invention relates to a process for recovering cumene. More particularly, the present invention relates to a process for recovering cumene, in which 2,3-dimethyl-2,3-diphenylbutane produced in a process in which cumene is used, is efficiently recovered as cumene.

BACKGROUND ART

As a process using cumene as a raw material for reaction, there are known a process having steps of converting cumene into cumene hydroperoxide and obtaining propylene oxide from such cumene hydroperoxide and propylene, aprocess of converting cumene into cumene hydroperoxide and obtaining phenol and acetone by subjecting such cumene hydroperoxide to acidolysis, and the like. In those processes, there is a reaction producing 2,3-dimethyl-2,3-diphenylbutane by dimerizing cumene as an undesirable side-reaction. By-production of 2,3-dimethyl-2,3-diphenylbutane causes undesirable effects such as consumption of cumene and obstruction to a desired reaction.

DISCLOSURE OF THE INVENTION

An object of the present invention is to provide a process for recovering cumene, in which 2,3-dimethyl-2,3-diphenylbutane produced in a process in which cumene is used, is efficiently recovered as cumene.

Namely, the present invention relates to a process for recovering cumene, which comprises:

subjecting 2,3-dimethyl-2,3-diphenylbutane produced in a process in which cumene is used, to hydrogenolysis in the presence of a catalyst thereby to it convert into cumene, and recovering cumene.

BEST MODE FOR CARRYING OUT THE INVENTION

As a process using cumene, there can be listed a process having steps of converting cumene into cumene hydroperoxide and obtaining propylene oxide from such cumene hydroperoxide and propylene, a process of converting cumene into cumene hydroperoxide and obtaining phenol and acetone by subjecting such cumene hydroperoxide to acidolysis, and the like.

The recovering process of the present invention is to recover cumene obtained by subjecting 2,3-dimethyl-2,3-diphenylbutane produced to hydrogenolysis in the presence of a catalyst thereby to convert it into cumene.

As the catalyst, a catalyst containing a metal of Group 10 or 11 of the Periodic Table (IUPAC Inorganic chemistry nomenclature, revised edition(1989)), is preferable. The metal is preferably at least one selected from the group consisting of copper, palladium, platinum and nickel. It is preferable to use a copper-based catalyst from the viewpoint of suppressing of by-products. As the copper-based catalyst, there can be listed copper, Raney copper, copper-chromium, copper-zinc, copper-chromium-zinc, copper-silica, copper-alumina, etc.

Hydrogenolysis can be carried out in a liquid phase or gas phase. A hydrogenolysis temperature is usually 0 to 500° C., and preferably 30 to 400° C. It is advantageous that a pressure is usually 100 to 10000 kPa. It is good that hydrogen exists equi-molar to 2,3-dimethyl-2,3-diphenylbutane or more. Hydrogenolysis can be advantageously carried out using a catalyst having a shape suitable for a slurry or fixed bed.

The process of the present invention can be conducted in batch, semi-continuous or continuous process.

When the process using cumene is a process having a step of obtaining propylene oxide from cumene hydroperoxide and propylene, it is preferable that hydrogenolysis is carried out after propylene oxide is separated and removed from the reaction products. When it is required to recover cumene from cumyl alcohol, hydrogenolysis can be also subjected to a reaction liquid containing cumyl alcohol as it is because cumyl alcohol produced in the step of obtaining propylene oxide from cumene hydroperoxide and propylene, is converted into cumene by hydrogenolysis, and when it is not desired to subject cumyl alcohol to hydrolysis, hydrolysis can be carried out after separating and removing cumyl alcohol. Hydrolysis can be carried out after separating and removing cumyl alcohol. It is preferable to carry out hydrolysis after separating-removing or concentrating 2,3-dimethyl-2,3-diphenylbutane from a view point of suppressing side-reactions of effective ingredients such cumene, cumyl alcohol and the like to a minimum.

When the process in which cumene is used, is a process for obtaining phenol and acetone by subjecting cumene hydroperoxide to acidolysis, it is preferable to carry out hydrolysis after separating and removing acetone and phenol to minimize losses caused to hydrogenation of acetone and nuclear-hydrogenation of phenol.

Cumene recovered can be used effectively in the same process or another process.

EXAMPLE

Example 1

A solution containing 1% by weight of 2,3-dimethyl-2,3-diphenylbutane was passed through a reactor filled with 16 cc of a copper-chromium catalyst (3 mm ø pellet) at a rate of 1 g/minute at a temperature of 220 to 260° C. under a pressure of 1 MPaG together with 300 cc/minute of hydrogen. Results were shown in Table 1.

TABLE 1

| Reaction temperature | 2,3-Dimethyl-2,3-diphenylbutane conversion *1 | Cumene selectivity *2 |
| --- | --- | --- |
| 220° C. | 84% | 100% |
| 240° C. | 97% | 100% |
| 260° C. | 100% | 100% |

*1: 2,3-Dimethyl-2,3-diphenylbutane conversion = converted 2,3-dimethyl-2,3-diphenylbutane (mol)/fed 2,3-dimethyl-2,3-diphenylbutane (mol) × 100
*2: Cumene selectivity = 0.5 × produced cumene (mol)/converted 2,3-dimethyl-2,3-diphenylbutane (mol) × 100

INDUSTRIAL APPLICABILITY

As described above, according to the present invention, a process for recovering cumene, in which 2,3-dimethyl-2,3-diphenylbutane produced in a process in which cumene is used, is efficiently recovered as cumene, can be provided.

What is claimed is:

1. A process for recovering cumene, which comprises:
   subjecting 2,3-dimethyl-2,3-diphenylbutane produced in a process in which cumene is used, to hydrogenolysis in the presence of a catalyst thereby to convert it into cumene, and
   recovering the cumene.

2. The process for recovering cumene according to claim 1, wherein the catalyst is a catalyst containing a metal of Group 10 or 11 of the periodic table.

3. The process for recovering cumene according to claim 1, the metal is at least one selected from the group consisting of copper, palladium, platinum and nickel.

4. The process for recovering cumene according to claim 1, wherein the process in which cumene is used, contains steps of converting cumene into cumene hydroperoxide and obtaining propylene oxide from the cumene hydroperoxide and propylene.

* * * * *